(12) United States Patent
Kim et al.

(10) Patent No.: US 11,485,692 B2
(45) Date of Patent: Nov. 1, 2022

(54) METHOD FOR PREPARING ETHYLENE

(71) Applicant: LG CHEM, LTD., Seoul (KR)

(72) Inventors: Tae Woo Kim, Daejeon (KR); Sung Kyu Lee, Daejeon (KR); In Seop Kim, Daejeon (KR); Joon Ho Shin, Daejeon (KR); Yeon Uk Choo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/647,828

(22) PCT Filed: Jul. 4, 2019

(86) PCT No.: PCT/KR2019/008197
§ 371 (c)(1),
(2) Date: Mar. 16, 2020

(87) PCT Pub. No.: WO2020/050484
PCT Pub. Date: Mar. 12, 2020

(65) Prior Publication Data
US 2020/0216373 A1 Jul. 9, 2020

(30) Foreign Application Priority Data
Sep. 4, 2018 (KR) .................. 10-2018-0105164

(51) Int. Cl.
*C07C 7/04* (2006.01)
*B01D 3/14* (2006.01)
*B01D 5/00* (2006.01)
*C07C 7/09* (2006.01)
*C07C 11/04* (2006.01)

(52) U.S. Cl.
CPC .............. *C07C 7/04* (2013.01); *B01D 3/143* (2013.01); *B01D 5/0003* (2013.01); *B01D 5/006* (2013.01); *C07C 7/09* (2013.01); *C07C 11/04* (2013.01)

(58) Field of Classification Search
None
See application file for complete search history.

(56) References Cited

U.S. PATENT DOCUMENTS

| 5,326,929 A | 7/1994 | Mehra et al. |
| 5,453,559 A | 9/1995 | Phillips et al. |
| 7,311,813 B2 * | 12/2007 | Reyneke ............ B01D 3/146 203/71 |

(Continued)

FOREIGN PATENT DOCUMENTS

| CN | 1715260 A | 1/2006 |
| CN | 108349849 A | 7/2018 |

(Continued)

*Primary Examiner* — Tam M Nguyen
(74) *Attorney, Agent, or Firm* — Dentons US LLP (57) ABSTRACT

A method for preparing ethylene including: feeding a thermally cracked compressed stream to a first distillation apparatus selectively operating as a first deethanizer or a depropanizer; and feeding an overhead discharge stream of the first distillation apparatus to a second distillation apparatus. When the first distillation apparatus is operated as the first deethanizer, a bottom discharge stream of the second distillation apparatus is fed to a C2 separator. When the first distillation apparatus is operated as the depropanizer, the bottom discharge stream of the second distillation apparatus is passed through a third distillation apparatus and fed to the C2 separator.

11 Claims, 2 Drawing Sheets

(56) References Cited

U.S. PATENT DOCUMENTS

| | | | |
|---|---|---|---|
| 2006/0004242 A1 | 1/2006 | Verma et al. | |
| 2006/0135840 A1* | 6/2006 | Reyneke | F25J 3/0233 |
| | | | 585/809 |
| 2006/0277943 A1 | 12/2006 | Yokohata et al. | |
| 2010/0025218 A1* | 2/2010 | Panditrao | C10G 45/00 |
| | | | 203/26 |
| 2014/0187840 A1 | 7/2014 | Fan et al. | |
| 2014/0303422 A1* | 10/2014 | Das | C07C 7/005 |
| | | | 585/809 |
| 2016/0319206 A1* | 11/2016 | Fritz | C07C 7/005 |
| 2018/0118639 A1* | 5/2018 | Al-Qahtani | B01J 8/08 |
| 2020/0071244 A1* | 3/2020 | Kim | C07C 7/04 |

FOREIGN PATENT DOCUMENTS

| | | |
|---|---|---|
| EP | 3 345 887 A1 | 7/2018 |
| JP | 7-507078 A | 8/1995 |
| JP | 2006188510 A | 7/2006 |
| KR | 10-0230672 B1 | 11/1999 |
| KR | 10-0338407 B1 | 5/2002 |
| KR | 10-2012-0094033 A | 8/2012 |
| KR | 10-2016-0085851 A | 7/2016 |
| KR | 10-2018-0084050 A | 7/2018 |
| WO | 2017195989 A1 | 11/2017 |

* cited by examiner

METHOD FOR PREPARING ETHYLENE

CROSS-REFERENCE TO RELATED APPLICATIONS

This application is the U.S. national stage of international Application No. PCT/KR2019/008197, filed on Jul. 4, 2019, and claims the benefit of priority to Korean Patent Application No. 10-2018-0105164, filed on Sep. 4, 2018, the disclosures of which are incorporated herein by reference in their entirety.

TECHNICAL FIELD

The present invention relates to an method for preparing ethylene, and more particularly, to an method for preparing ethylene capable of increasing yield of ethylene by preventing an overload due to an increase in production amount when ethylene is produced by a thermal cracking method.

BACKGROUND

In general, ethylene has been produced by various methods such as a method of thermal cracking naphtha, ethane, propane, and the like, a method of hydrogenating acetylene, a method of dehydrating alcohol, and the like. Among these methods, in the thermal cracking method, a hydrocarbon compound such as naphtha and the like as a feedstock are input to a furnace, the hydrocarbon compound is subjected to thermal cracking in the furnace, and the thermally cracked product is subjected to cooling, compression, and purification.

In recent years, in a thermal cracking method using a hydrocarbon compound such as naphtha and the like as a feedstock, in order to an increase yield of product such as ethylene, a method including a gas phase decomposition step in which ethane, propane, and the like are used as a feedstock in addition to a liquid phase decomposition step in which naphtha is used as a feedstock has been used. Here, as ethane, in a thermally cracked product generated by cracking of naphtha, ethane circulated after purification is used as a feedstock, and as propane, in the thermally cracked product generated by cracking of naphtha, propane circulated after purification is used as a feedstock, or propane introduced from the outside is used as a feedstock. In particular, since propane is cheaper than other feedstocks, it may be easily obtained and the cost of production may be lowered.

Meanwhile, in a case where a gas phase decomposition step using ethane, propane, and the like is added to a naphtha thermal cracking process, it is preferable that processes for cooling, compressing, and purifying the product generated from thermal cracking are added, but only a furnace is added due to a problem such as a space for additionally providing the other processes.

However, in a case where an additional furnace is installed and additional propane is introduced from the outside to be used as a feedstock in the furnace, a difference in cracking yield between the additional propane and existing ethane circulated and reused as a feedstock is very large. In particular, in a case where a proportion of the thermal cracking process in which propane is used as a feedstock is increased, such as a case where an additional furnace using propane as a feedstock is installed, a case where the liquid phase decomposition step in which naphtha is used is interrupted due to maintenance of process equipment, or the like, a content of methane in the product generated by thermal cracking is extremely increased, resulting in an occurrence of an overload in a purification process.

SUMMARY

In order to solve the problems mentioned in the background art, an object of the present invention is to provide an method for preparing ethylene capable of coping with a change in a cracking yield depending on a change in the type of feedstock when ethylene is produced by thermal cracking of naphtha.

That is, an object of the present invention is to provide an method for preparing ethylene capable of coping with a change in a cracking yield depending on a change in the type of feedstock when ethylene is produced by thermal cracking of naphtha so that an additional gas furnace in which a gas phase feedstock is used may be freely installed, and may be individually operated even in a case where the liquid phase decomposition step in which naphtha is used is interrupted due to maintenance of process equipment.

In addition, another object of the present invention is to provide an method for preparing ethylene capable of producing ethylene with less energy consumption, even though a content of methane in the thermally cracked compressed stream is increased, by relatively reducing the amount of work increasing in proportion to a production amount while increasing yield of ethylene by addition of a feedstock, when ethylene is produced by thermal cracking of naphtha.

In one general aspect, an method for preparing ethylene includes: feeding a thermally cracked compressed stream to a first distillation apparatus selectively operated as a first deethanizer or a depropanizer; and feeding an overhead discharge stream of the first distillation apparatus to a second distillation apparatus, wherein in a case where the first distillation apparatus is operated as the first deethanizer, a bottom discharge stream of the second distillation apparatus is fed to a C2 separator, and in a case where the first distillation apparatus is operated as the depropanizer, the bottom discharge stream of the second distillation apparatus is passed through a third distillation apparatus and fed to the C2 separator.

In a case where ethylene is produced using the method for preparing ethylene according to the present invention, it is possible to cope with a change in a cracking yield depending on a change in the type of feedstock, such that an additional gas furnace in which a gas phase feedstock is used may be freely installed, and may be individually operated even in a case where the liquid phase decomposition step in which naphtha is used is interrupted due to maintenance of process equipment.

In addition, in a case where ethylene is produced using the method for preparing ethylene according to present invention, since the amount of work increasing in proportion to a production amount is relatively reduced while increasing yield of ethylene by addition of a feedstock, it is possible to produce ethylene with less energy consumption even though a content of methane in the thermally cracked compressed stream is increased.

DETAILED DESCRIPTION

The terms and words used in the description and claims of the present invention are not to be construed as a general or dictionary meanings but are to be construed as meanings and concepts meeting the technical ideas of the present invention based on a principle that the inventors can appropriately define the concepts of terms in order to describe their own inventions in the best mode.

In the present invention, the term "stream" may mean a flow of a fluid in a process and may also mean a fluid itself flowing through a pipe. Specifically, the "stream" may mean both a fluid itself flowing through a pipe connecting respective apparatuses and a flow of the fluid. In addition, the fluid may mean gas or liquid.

Hereinafter, the present invention will be described in more detail for understanding the present invention.

Figure 2:
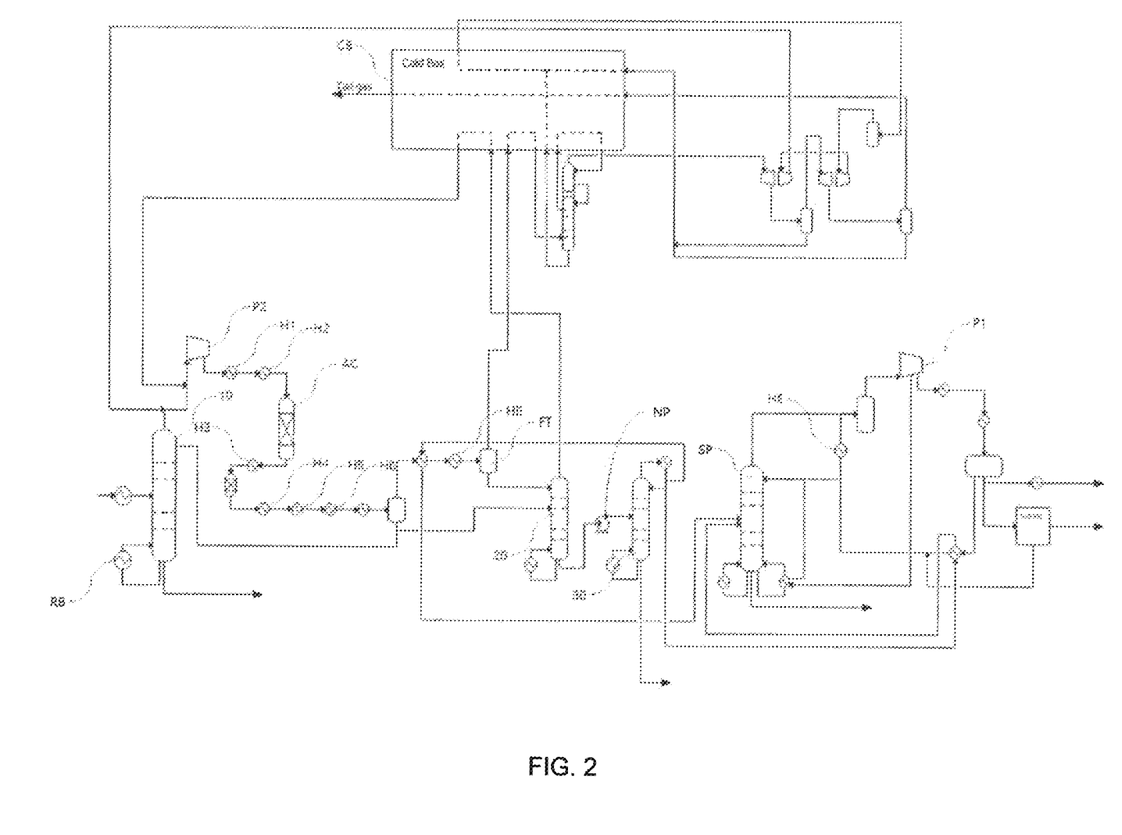
FIG. 2 is a process flow diagram according to an embodiment of this application.

An method for preparing ethylene according to the present invention may include: a thermal cracking process of inputting naphtha, recycled C2 and C3 hydrocarbon compounds, and propane as a feedstock to respective furnaces and performing thermal cracking in the respective furnaces (S1, not illustrated); a cooling process of cooling thermally cracked gas which is obtained from the thermal cracking in the respective furnaces and contains hydrogen and C1, C2, and C3+ hydrocarbon compounds (S2, not illustrated); a compression process of compressing the cooled thermally cracked gas (S3, not illustrated); and a purification process of purifying a thermally cracked compressed stream containing hydrogen and C1, C2, and C3+ hydrocarbon compounds (S4, illustrated in FIG. 2).

Specifically, the thermal cracking process (S1) may include: a liquid phase decomposition step in which naphtha is used as a feedstock; a gas phase decomposition step in which recycled C2 and C3 hydrocarbon compounds such as ethane, propane, and the like are used as a feedstock; and a gas phase decomposition step in which propane is used as a feedstock.

The cooling process (S2) may include a cooling step of cooling the thermally cracked gas generated in the respective furnaces in the thermal cracking process (S1) in a cooling tower.

The compression process (S3) may include a compression step of compressing the cooled thermally cracked stream in the cooling process (S2) through multistage compression by two or more compressors to purify the cooled thermally cracked stream.

As illustrated in FIG. 2, the purification process (S4) includes: feeding a thermally cracked compressed stream to a first distillation apparatus 10 selectively operated as a first deethanizer or a depropanizer; and feeding an overhead discharge stream of the first distillation apparatus 10 to a second distillation apparatus 20, in which in a case where the first distillation apparatus 10 is operated as the first deethanizer, a bottom discharge stream of the second distillation apparatus 20 is fed to a C2 separator SP, and in a case where the first distillation apparatus 10 is operated as the depropanizer, the bottom discharge stream of the second distillation apparatus 20 is passed through a third distillation apparatus 30 and fed to the C2 separator SP.

Specifically, in the thermal cracking process (S1), in a case where ethylene is produced through a gas phase decomposition step in which propane is used as a feedstock, since propane is cheaper than other feedstocks, as compared to a case in which naphtha and recycled C2 and C3 hydrocarbon compounds are used as a feedstock, it may be easily obtained from the outside and may be effective in lowering the cost of production and increasing yield of ethylene.

However, in a case of adding propane as a feedstock, as compared to a case where a content of methane in the thermally cracked gas obtained by thermal cracking of recycled ethane which is used as a feedstock is about 10 mole %, a content of methane in the thermally cracked gas generated in the thermal cracking process (S1) is sharply increased to about 20 mole %, which is problematic. As such, when the content of methane in the thermally cracked gas is increased, in the purification process (S4), a boiling point of a mixture including hydrogen and a hydrocarbon compound in all streams containing methane is lowered.

Figure 1:
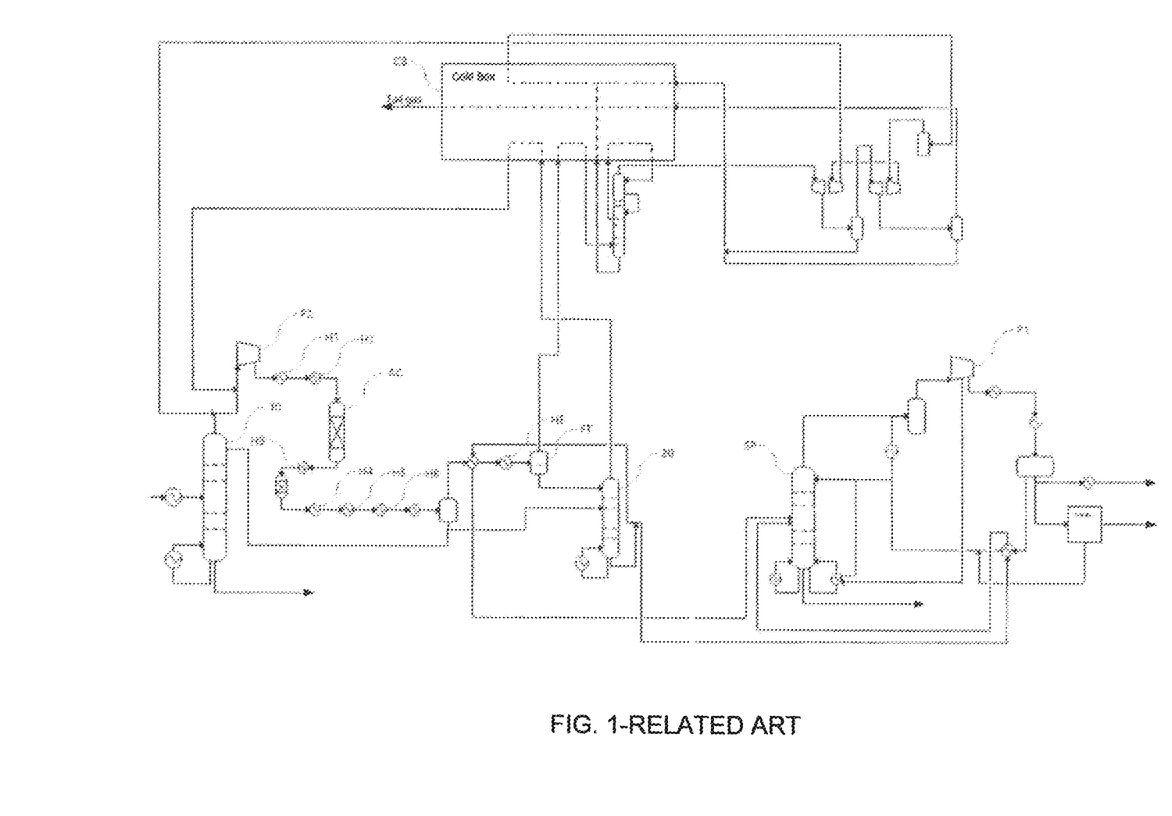
FIG. 1 is a process flow diagram according to a method for preparing ethylene according to related art.

Accordingly, as illustrated in FIG. 1, in a case where a thermally cracked compressed stream is fed to a first distillation apparatus 10 operated as a deethanizer, an overhead discharge stream of the first distillation apparatus 10 is fed to a second distillation apparatus 20, and a bottom discharge stream of the second distillation apparatus 20 is fed to a C2 separator SP, it is difficult to sufficiently condense the overhead discharge stream of the first distillation apparatus 10 with only a refrigerant of a heat exchanger HE.

Therefore, since a flow rate of an overhead discharge stream of a gas-liquid separator FT provided in the front of the second distillation apparatus 20 is significantly increased before the overhead discharge stream of the first distillation apparatus 10 is fed to the second distillation apparatus 20, a loss of ethylene occurs. In addition, an overload occurs on a cold box CB. As a result, it is difficult to secure a circulation from the cold box CB to the first distillation apparatus 10.

On the other hand, according to the method for preparing ethylene of the present invention, in the purification process (S4), in a case where the third distillation apparatus 30 is additionally installed and the first distillation apparatus 10 is selectively operated, it is possible to sufficiently condense the overhead discharge stream of the first distillation apparatus 10 to be fed to the second distillation apparatus 20 in the heat exchanger HE. In addition, accordingly, in the overhead discharge stream of the gas-liquid separator FT provided in the front of the second distillation apparatus 20, a content of methane circulated to the cold box CB is easily adjusted, which is effective in preventing an overload in the purification process. Therefore, since the amount of work increasing in proportion to a production amount is relatively reduced, it is possible to produce ethylene with less energy consumption even though a content of methane in the thermally cracked compressed stream is increased.

According to an embodiment of the present invention, the first distillation apparatus 10 may be an apparatus for distilling and separating the thermally cracked compressed stream. The first distillation apparatus 10 may be selectively operated as a first deethanizer or a depropanizer. In this case, the first distillation apparatus 10 may be selectively operated as the first deethanizer or the depropanizer depending on a component of the thermally cracked compressed stream.

Specifically, the first distillation apparatus 10 may be selectively operated depending on a content of a C1 hydrocarbon compound of the thermally cracked compressed stream to be fed to the first distillation apparatus 10 in order to sufficiently condense the overhead discharge stream of the first distillation apparatus 10 to be fed to the second distillation apparatus 20 in the heat exchanger HE.

More specifically, in a case where a content of a C1 hydrocarbon compound in the thermally cracked compressed stream is less than 20 mole %, the first distillation apparatus 10 may be operated as the first deethanizer, and in a case where the content of the C1 hydrocarbon compound in the thermally cracked compressed stream is 20 mole % or more, the first distillation apparatus 10 may be operated as the depropanizer.

In a case where the content of the C1 hydrocarbon compound in the thermally cracked compressed stream to be fed to the first distillation apparatus 10 is increased, it is difficult to sufficiently condense the overhead discharge stream of the first distillation apparatus 10 in the heat exchanger HE. However, as in the present invention, in the case where the content of the C1 hydrocarbon compound in the thermally cracked compressed stream is 20 mole % or more, the first distillation apparatus 10 may be selectively operated as the depropanizer, such that it is possible to increase a boiling point of the entire overhead discharge stream of the first distillation apparatus 10.

Therefore, even though the content of the C1 hydrocarbon compound in the thermally cracked compressed stream is increased depending on the type of feedstock in the thermal cracking process (S1), it is possible to sufficiently condense the overhead discharge stream of the first distillation apparatus 10 to be fed to the second distillation apparatus 20 in the heat exchanger HE, which is effective in preventing the overload in the purification process.

Meanwhile, according to an embodiment of the present invention, the first distillation apparatus 10 may be selected as the first deethanizer or the depropanizer depending on an operation condition of the first distillation apparatus 10. In the case where the first distillation apparatus 10 is selectively operated as the first deethanizer, an operation temperature of the first distillation apparatus 10 may be −80° C. to 40° C., −70° C. to 30° C., or −65° C. to 20° C. In the case where the first distillation apparatus 10 is selectively operated as the depropanizer, an operation temperature of the first distillation apparatus 10 may be −50° C. to 90° C., −40° C. to 80° C., or −20° C. to 60° C.

In addition, according to an embodiment of the present invention the operation temperature of the first distillation apparatus 10 selectively operated as the first deethanizer or the depropanizer may be adjusted by a reboiler RB provided near a lower portion of the first distillation apparatus 10.

According to an embodiment of the present invention, the reboiler provided near the lower portion of the first distillation apparatus 10 may use a heat source, which is for adjusting the operation temperature of the first distillation apparatus 10, supplied from the outside, such as quench water, steam, or the like.

According to an embodiment of the present invention, the thermally cracked compressed stream to be fed to the first distillation apparatus 10 may contain hydrogen and C1, C2, and C3+ hydrocarbon compounds. The thermally cracked compressed stream fed to the first distillation apparatus 10 may be separated and purified differently depending on the selected first distillation apparatus 10.

According to an embodiment of the present invention, in the case where the first distillation apparatus 10 is selectively operated as the first deethanizer, the first distillation apparatus 10 may separate and purify a C3+ hydrocarbon compound from the thermally cracked compressed stream. Specifically, the overhead discharge stream of the first distillation apparatus 10, that is, an overhead discharge stream of the first deethanizer separated, purified, and discharged from the first deethanizer may contain hydrogen and C1 and C2 hydrocarbon compounds, and a bottom discharge stream of the first deethanizer may contain a C3+ hydrocarbon compound.

In addition, according to an embodiment of the present invention, in the case where the first distillation apparatus 10 is selectively operated as the depropanizer, the first distillation apparatus 10 may separate and purify a C4+ hydrocarbon compound from the thermally cracked compressed stream. Specifically, an overhead discharge stream of the first distillation apparatus 10, that is, the overhead discharge stream of the depropanizer separated, purified, and discharged from the depropanizer may contain hydrogen and C1, C2, and C3 hydrocarbon compounds, and a bottom discharge stream of the depropanizer may contain a C4+ hydrocarbon compound.

That is, according to an embodiment of the present invention, as described above, a component of the overhead discharge stream of the first distillation apparatus 10 may vary depending on the type of the first distillation apparatus 10 to be selectively operated, that is, the first deethanizer or the depropanizer. Therefore, even though the content of the C1 hydrocarbon compound in the thermally cracked compressed stream is increased while the first distillation apparatus 10 is selectively operated as the first deethanizer, when the operation of the first distillation apparatus 10 is converted into the depropanizer and the depropanizer is operated at a lower boiling point, it is possible to sufficiently condense the overhead discharge stream of the first distillation apparatus 10 in the same heat exchanger HE. As a result, it is possible to flexibly perform the purification process of the thermally cracked compressed stream depending on a change in the type of feedstock.

In addition, according to an embodiment of the present invention, the bottom discharge stream of the first deethanizer may be fed to a depropanizer (not illustrated), a bottom discharge stream of the depropanizer may be fed to a debutanizer (not illustrated), and thereafter, a process of purifying and separating a C3+ or C4+ hydrocarbon compound may be performed in each of the depropanizer (not illustrated) or the debutanizer (not illustrated).

Meanwhile, according to an embodiment of the present invention, the method for preparing ethylene may further include: feeding the overhead discharge stream of the first distillation apparatus 10 to a second compressor P2 before the overhead discharge stream of the first distillation apparatus 10 is fed to the second distillation apparatus 20; feeding a compressed discharge stream of the second compressor P2 to an acetylene converter AC; and feeding a bottom discharge stream of the acetylene converter AC to the second distillation apparatus 20.

According to an embodiment of the present invention, the multistage compression in the compression process (S3) may be performed by four-stage compressors (a fourth compressor is represented by P2 in FIG. 2 and the first to third compressors positioned in the front of the fourth compressor are not illustrated).

Specifically, in the compression process (S3), first- to third-stage compressions are performed, and the thermally cracked compressed stream including hydrogen and C1, C2, and C3+ hydrocarbon compounds which is compressed and discharged at the third-stage compressor may be fed to the first distillation apparatus 10 of the purification process (S4).

As described above, the thermally cracked compressed stream fed to the first distillation apparatus 10 may be purified and separated into the overhead discharge stream and the bottom discharge stream of the first distillation apparatus 10, the overhead discharge stream of the first distillation apparatus 10 is fed to the second compressor P2 which is the fourth compressor among the four-stage compressors, and the four-stage compressions may be performed in the purification process (S4). In this case, it is possible to reduce the amount of hydrocarbon compound introduced into the second compressor P2 which is the fourth compressor among the four-stage compressors, as compared to a case where first- to fourth-stage compressions are performed in the compression process, (S3) and then the compressed stream is introduced in the purification process (S4). Therefore, it is possible to save operation energy in the process.

In addition, in the purification process (S4), the thermally cracked compressed stream may be cooled by one or more heat exchangers before being fed to the first distillation apparatus 10, the compressed discharge stream of the second compressor P2 may be cooled by one or more heat exchangers H1 and H2 before being fed to the acetylene converter AC, and the bottom discharge stream of the acetylene converter AC may be cooled by one or more heat exchangers H3, H4, H5, and H6, may be dried by one or more driers, and may be separated into a part of the stream by one or more gas-liquid separators, before being fed to the heat exchanger HE and the gas-liquid separator FT which are provided in the front of the second distillation apparatus 20.

According to an embodiment of the present invention, the heat exchanger HE and the gas-liquid separator FT may be provided in the front of the second distillation apparatus 20.

According to an embodiment of the present invention, the heat exchanger HE may cool the overhead discharge stream of the first distillation apparatus 10 or the bottom discharge stream of the acetylene converter AC. The overhead discharge stream of the first distillation apparatus 10 or the bottom discharge stream of the acetylene converter AC passing through the heat exchanger HE is cooled by the heat exchanger HE, and may be fed to the gas-liquid separator FT in a condensed state.

In addition, according to an embodiment of the present invention, the overhead discharge stream of the first distillation apparatus 10 or the bottom discharge stream of the acetylene converter AC passed through the heat exchanger HE and fed to the gas-liquid separator FT may be subjected to gas-liquid separation into an overhead discharge stream and a bottom discharge stream of the gas-liquid separator FT.

According to an embodiment of the present invention, the bottom discharge stream of the gas-liquid separator FT may be fed to the second distillation apparatus 20. At this time, in the case where the first distillation apparatus 10 is the first deethanizer depending on the type of the first distillation apparatus 10, the bottom discharge stream of the gas-liquid separator FT may contain hydrogen and C1 and C2 hydrocarbon compounds, and in the case where the first distillation apparatus 10 is the depropanizer depending on the type of the first distillation apparatus 10, the bottom discharge stream of the gas-liquid separator FT may contain hydrogen and C1, C2, and C3 hydrocarbon compounds.

According to an embodiment of the present invention, the overhead discharge stream of the gas-liquid separator FT may be circulated to the cold box CB, and the overhead discharge stream of the gas-liquid separator FT may contain hydrogen and a C1 hydrocarbon compound. In addition, the overhead discharge stream of the gas-liquid separator FT may contain a part of a C2 or C3 hydrocarbon compound.

Meanwhile, according to an embodiment of the present invention, the second distillation apparatus 20 may be a demethanizer and the third distillation apparatus 30 may be a second deethanizer.

According to an embodiment of the present invention, in the case where the first distillation apparatus 10 is operated as the first deethanizer depending on the type of the first distillation apparatus 10, the second distillation apparatus 20 may purify and separate hydrogen, a C1 hydrocarbon compound, and a C2 hydrocarbon compound, and in the case where the first distillation apparatus 10 is operated as the depropanizer depending on the type of the first distillation apparatus 10, the second distillation apparatus 20 may purify and separate hydrogen, a C1 hydrocarbon compound, and C2 and C3 hydrocarbon compounds. Specifically, the overhead discharge stream of the first distillation apparatus 10 fed to the second distillation apparatus 20 may be purified and separated into an overhead discharge stream and a bottom discharge stream of the second distillation apparatus 20 in the second distillation apparatus 20.

According to an embodiment of the present invention, regardless of the type of the first distillation apparatus 10, the overhead discharge stream of the second distillation apparatus 20 may contain hydrogen and a C1 hydrocarbon compound, and the overhead discharge stream of the second distillation apparatus 20 may be circulated to the cold box CB. As described above, a part of the overhead discharge stream of the second distillation apparatus 20 circulated to the cold box CB is passed through the cold box CB, and may be discharged through a tail gas or may be circulated to the first distillation apparatus 10 from the cold box CB.

According to an embodiment of the present invention, in the case where the first distillation apparatus 10 is operated as the first deethanizer, the bottom discharge stream of the second distillation apparatus 20 may be fed to the C2 separator SP. In this case, the bottom discharge stream of the second distillation apparatus 20 may contain only a C2 hydrocarbon compound, and as a specific example, the bottom discharge stream of the second distillation apparatus 20 may contain ethane and ethylene. In addition, according to an embodiment of the present invention, the part of the bottom discharge stream of the second distillation apparatus 20 is passed through the heat exchanger and may be fed to the C2 separator SP, and a residue of the bottom discharge stream of the second distillation apparatus 20 may be directly fed to the C2 separator SP.

According to an embodiment of the present invention, in the case where the first distillation apparatus 10 is operated as the depropanizer, the bottom discharge stream of the second distillation apparatus 20 may be fed to the third distillation apparatus 30. In this case, the bottom discharge stream of the second distillation apparatus 20 may contain C2 and C3 hydrocarbon compounds. In addition, the bottom discharge stream of the second distillation apparatus 20 may be fed to the third distillation apparatus 30 by a pump NP.

According to an embodiment of the present invention, the third distillation apparatus 30 may purify and separate the C2 hydrocarbon compound and the C3 hydrocarbon compound from the bottom discharge stream of the second distillation apparatus 20. Specifically, the bottom discharge stream of the second distillation apparatus 20 fed to the third distillation apparatus 30 may be purified and separated into an overhead discharge stream and a bottom discharge stream of the third distillation apparatus 30 in the third distillation apparatus 30.

According to an embodiment of the present invention, the overhead discharge stream of the third distillation apparatus 30 may be fed to the C2 separator SP. In this case, the overhead discharge stream of the third distillation apparatus 30 may be a mixture of C2 hydrocarbon compounds, as a specific example, the overhead discharge stream of the third distillation apparatus 30 may contain only a C2 hydrocarbon compound, and as a more specific example, the overhead discharge stream of the third distillation apparatus 30 may contain ethane and ethylene. In addition, according to an embodiment of the present invention, the part of the overhead discharge stream of the third distillation apparatus 30 is passed through the heat exchanger and may be fed to the C2 separator SP, and a residue of the overhead discharge stream of the third distillation apparatus 30 may be directly fed to the C2 separator SP.

According to an embodiment of the present invention, the bottom discharge stream of the third distillation apparatus 30 may be fed to a C3 separator SP (not illustrated). In this case, the bottom discharge stream of the third distillation apparatus 30 may be a mixture of C3 hydrocarbon compounds, as a specific example, the bottom discharge stream of the third distillation apparatus 30 may contain only a C3 hydrocarbon compound, and as a more specific example, the bottom discharge stream of the third distillation apparatus 30 may contain propane, propylene, and propyne. The C3 hydrocarbon compound separated and purified in the C3 separator (not illustrated) may be obtained as a product or circulated as a feedstock depending on the type and need.

In addition, according to an embodiment of the present invention, the C2 separator SP may purify and separate a C2 hydrocarbon compound. Specifically, the bottom discharge stream of the second distillation apparatus 20 or the overhead discharge stream of the third distillation apparatus 30 fed to the C2 separator SP may be purified and separated into the overhead discharge stream and the bottom discharge stream of the C2 separator SP in the C2 separator SP.

According to an embodiment of the present invention, the overhead discharge stream of the C2 separator SP may contain ethylene, and the overhead discharge stream of the C2 separator SP may be fed to the first compressor P1.

According to an embodiment of the present invention, the bottom discharge stream of the C2 separator SP may contain ethane, and the bottom discharge stream of the C2 separator SP may be circulated as the feedstock in the thermal cracking process (S1).

According to an embodiment of the present invention, the first compressor P1 is used for producing ethylene from the overhead discharge stream of the C2 separator SP, and may be a so-called ethylene refrigerant compressor (ERC). The compressed discharge stream of the first compressor P1 may include a first circulation flow, a second circulation flow, and a third circulation flow.

According to an embodiment of the present invention, the first circulation flow may be a flow in which a part of the compressed discharge stream of the first compressor P1 is passed through the heat exchanger HE and fed to the first compressor P1.

In addition, according to an embodiment of the present invention, the second circulation flow may be a flow in which a part of the compressed discharge stream of the first compressor P1 is circulated to the C2 separator SP.

In addition, according to an embodiment of the present invention, the third circulation flow may be a flow in which a part of the compressed discharge stream of the first compressor P1 obtains ethylene as a product.

According to an embodiment of the present invention, the part of the compressed discharge stream of the first compressor P1 is the first circulation flow, and may be passed through the heat exchanger HE and fed to the first compressor P1. The first circulation flow may be used as a refrigerant stream of the heat exchanger HE while passing through the heat exchanger HE. In this regard, in FIG. 2, although the heat exchangers HEs are illustrated in the front of the gas-liquid separator FT and the front of the first compressor P1, respectively, for convenience of description and illustration, the heat exchanger HE provided in the front of the gas-liquid separator FT and the heat exchanger HE provided in the front of the first compressor P1 may be identical to each other.

According to the method for preparing ethylene of the present invention, heat between the overhead discharge stream of the first distillation apparatus 10 or the bottom discharge stream of the acetylene converter AC passing through the heat exchanger HE and the first circulation flow may be exchanged in the heat exchanger HE by a countercurrent flow, a co-current flow, or a cross flow. In this case, the first circulation flow is used as a refrigerant stream and may cool the overhead discharge stream of the first distillation apparatus 10 or the bottom discharge stream of the acetylene converter AC.

Meanwhile, according to an embodiment of the present invention, a temperature of the part of the compressed discharge stream of the first compressor P1 forming the first circulation flow is required to be lowered to be used as the refrigerant stream before passing through the heat exchanger HE, and the temperature may be lowered by adjusting a pressure of the part of the compressed discharge stream of the first compressor P1 forming the first circulation flow.

In addition, according to an embodiment of the present invention, the first circulation flow after passing through the heat exchanger HE is joined to the overhead discharge stream of the C2 separator SP and may be fed to the first compressor P1.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXPERIMENTAL EXAMPLES

Example 1

The process of the process flow diagram illustrated in FIG. 2 was simulated using the ASPEN Plus simulator produced by Aspen Technology, Inc.

As a feedstock of the thermal cracking process (S1), a recycled C2 hydrocarbon compound with a flow rate of 31,606 kg/hr, a recycled C3 hydrocarbon compound with a flow rate of 6,102 kg/hr, and propane supplied from the outside with a flow rate of 18,506 kg/hr were used. The composition of the thermally cracked compressed stream is shown in Table 1, the temperatures and pressures of the respective streams in the purification process (S4) are shown in Table 2, and the composition of the overhead discharge stream and the flow rate of the gas-liquid separator FT are shown in Table 3. At this time, as shown in Table 1, since the content of methane in the composition of the thermally cracked compressed stream was 14.6 mole % which is less than 20 mole %, the first distillation apparatus 10 was operated as the first deethanizer, the third distillation apparatus 30 was not operated, and the bottom discharge stream of the second distillation apparatus 20 was directly fed to the C2 separator SP.

TABLE 1

| Classification | Content (mole %) |
|---|---|
| Hydrogen | 29.7 |
| Methane | 14.6 |
| Ethane | 15.1 |
| Ethylene | 32.7 |
| Acetylene | 0.4 |

TABLE 1-continued

| Classification | Content (mole %) |
| --- | --- |
| Propane | 2.2 |
| Propylene | 3.4 |
| C4+ | 1.9 |

TABLE 2

| Classification | Temperature (° C.) | Pressure (kg/cm²G) |
| --- | --- | --- |
| Thermally cracked compressed stream containing hydrogen and C1, C2, and C3+ hydrocarbon compounds | −21 | 7.50 |
| Overhead discharge stream of first distillation apparatus 10 | −64.4 | 7.20 |
| Compressed discharge stream of second compressor P2 | 34.5 | 28.54 |
| Bottom discharge stream of acetylene converter AC | 77.7 | 25.29 |
| Bottom discharge stream of acetylene converter AC after passing through heat exchanger HE | −71.1 | 23.05 |
| Bottom discharge stream of gas-liquid separator FT | −71.2 | 22.91 |
| Overhead discharge stream of second distillation apparatus 20 | −71.7 | 9.30 |
| Bottom discharge stream of second distillation apparatus 20 | −45.2 | 9.60 |
| Overhead discharge stream of third distillation apparatus 30 | — | — |
| Bottom discharge stream of third distillation apparatus 30 | — | — |
| Overhead discharge stream of C2 separator SP | −73.9 | 3.47 |
| Bottom discharge stream of C2 separator SP | −52.6 | 4.10 |
| Compressed discharge stream of first compressor P1 | 31 | 18.85 |
| First circulation flow (refrigerant stream) before passing through heat exchanger HE | −74.9 | 3.34 |
| First circulation flow (refrigerant stream) after passing through heat exchanger HE | −74.8 | 3.31 |

TABLE 3

| Classification | Content (mole %) |
| --- | --- |
| Hydrogen | 45.8 |
| Methane | 33.3 |
| Ethane | 3.5 |
| Ethylene | 17.4 |
| Propane | 0 |
| Propylene | 0 |
| Flow rate | 20,669 (kg/hr) |

Example 2

In Example 1, as a feedstock of the thermal cracking process (S1), a recycled C2 hydrocarbon compound with a flow rate of 32,740 kg/hr, a recycled C3 hydrocarbon compound with a flow rate of 16,869 kg/hr, and propane supplied from the outside with a flow rate of 79,561 kg/hr were used. The composition of the thermally cracked compressed stream is shown in Table 4, the temperatures and pressures of the respective streams in the purification process (S4) are shown in Table 5, and the composition of the overhead discharge stream and the flow rate of the gas-liquid separator FT are shown in Table 6. At this time, as shown in Table 4, since the content of methane in the composition of the thermally cracked compressed stream was 26.0 mole % which is 20 mole % or more, the first distillation apparatus 10 was operated as the depropanizer, the third distillation apparatus 30 was operated, and the bottom discharge stream of the second distillation apparatus 20 was passed through the third distillation apparatus 30 and fed to the C2 separator SP.

TABLE 4

| Classification | Content (mole %) |
| --- | --- |
| Hydrogen | 20.4 |
| Methane | 26.0 |
| Ethane | 7.6 |
| Ethylene | 31.4 |
| Acetylene | 0.4 |
| Propane | 5.7 |
| Propylene | 6.5 |
| C4+ | 2.0 |

TABLE 5

| Classification | Temperature (° C.) | Pressure (kg/cm²G) |
| --- | --- | --- |
| Thermally cracked compressed stream containing hydrogen and C1, C2, and C3+ hydrocarbon compounds | −37 | 7.50 |
| Overhead discharge stream of first distillation apparatus 10 | −39.8 | 7.21 |
| Compressed discharge stream of second compressor P2 | 42.3 | 28.54 |
| Bottom discharge stream of acetylene converter AC | 82.6 | 26.86 |
| Bottom discharge stream of acetylene converter AC after passing through heat exchanger HE | −72.0 | 23.05 |
| Bottom discharge stream of gas-liquid separator FT | −72.2 | 22.84 |
| Overhead discharge stream of second distillation apparatus 20 | −78.9 | 9.30 |
| Bottom discharge stream of second distillation apparatus 20 | −38.3 | 9.60 |
| Overhead discharge stream of third distillation apparatus 30 | −19.0 | 23.00 |
| Bottom discharge stream of third distillation apparatus 30 | 61.4 | 23.47 |
| Overhead discharge stream of C2 separator SP | −73.9 | 3.47 |
| Bottom discharge stream of C2 separator SP | −52.6 | 4.1 |
| Compressed discharge stream of first compressor P1 | 31.1 | 18.85 |
| First circulation flow (refrigerant stream) before passing through heat exchanger HE | −74.6 | 3.34 |
| First circulation flow (refrigerant stream) after passing through heat exchanger HE | −74.9 | 3.30 |

TABLE 6

| Classification | Content (mole %) |
| --- | --- |
| Hydrogen | 26.4 |
| Methane | 55.2 |

TABLE 6-continued

| Classification | Content (mole %) |
| --- | --- |
| Ethane | 1.8 |
| Ethylene | 16.4 |
| Propane | 0.1 |
| Propylene | 0.1 |
| Flow rate | 64,869 (kg/hr) |

Comparative Example

The processes were simulated under the same conditions as in Example 2, except that the process flow diagram illustrated in FIG. 1 was used instead of the process flow diagram illustrated in FIG. 2. The flow rate and composition of the thermally cracked compressed stream to be fed to the first distillation apparatus is the same as shown in Table 4.

The temperatures and pressures of the respective streams in the purification process (S4) are shown in Table 7 and the composition and the flow rate of the overhead discharge stream of the gas-liquid separator FT are shown in Table 8.

TABLE 7

| Classification | Temperature (° C.) | Pressure (kg/cm²G) |
| --- | --- | --- |
| Thermally cracked compressed stream containing hydrogen and C1, C2, and C3+ hydrocarbon compounds | −21 | 7.5 |
| Overhead discharge stream of first distillation apparatus 10 | −67.8 | 7.21 |
| Compressed discharge stream of second compressor P2 | 35.8 | 28.54 |
| Bottom discharge stream of acetylene converter AC | 77.7 | 25.29 |
| Bottom discharge stream of acetylene converter AC after passing through heat exchanger HE | −80.9 | 23.05 |
| Bottom discharge stream of gas-liquid separator FT | −81.0 | 22.91 |
| Overhead discharge stream of gas-liquid separator FT | −81.0 | 22.91 |
| Overhead discharge stream of second distillation apparatus 20 | −91.2 | 9.3 |
| Bottom discharge stream of second distillation apparatus 20 | −53.3 | 9.6 |
| Overhead discharge stream of C2 separator SP | −74.2 | 3.47 |
| Bottom discharge stream of C2 separator SP | −52.5 | 4.1 |
| Compressed discharge stream of first compressor P1 | 27.5 | 18.85 |
| First circulation flow (refrigerant stream) before passing through heat exchanger HE | −70.6 | 4.3 |

TABLE 8

| Classification | Content (mole %) |
| --- | --- |
| Hydrogen | 30.8 |
| Methane | 56.5 |
| Ethane | 1.1 |
| Ethylene | 11.6 |
| Flow rate | 50,464 (kg/hr) |

As shown in Tables 1 and 4, it was confirmed that in a case where, in the thermal cracking process (S1), a flow rate of propane which is used as a feedstock is increased as in Example 2, the content of methane in the thermally cracked compressed stream was increased.

In addition, as shown in Tables 6 and 8, it was confirmed that in a case where the feedstocks of the same type are fed at the same flow rates, in the purification process (S4), as compared to Comparative Example in which the first distillation apparatus 10 is used as only the deethanizer, in Example 2 in which the first distillation apparatus 10 is used as the depropanizer depending on the content of methane in the thermally cracked compressed stream, it was possible to sufficiently condense the bottom discharge stream of the acetylene converter AC after passing through the heat exchanger HE, and adjust the content of methane discharged through the overhead discharge stream of the gas-liquid separator FT circulated to the cold box CB, such that the overload on the cold box CB was prevented and the circulation from the cold box CB to the first distillation apparatus 10 was secured.

In addition, the temperature and the pressure of each of the stream shown in Table 7 correspond to a temperature and a pressure for performing the process simulation according to the process flow diagram illustrated in FIG. 1. However, in a case of the bottom discharge stream of the acetylene converter AC after passing through the heat exchanger HE of Table 7, since the actual process is performed in a system in which the lowest temperature is −75° C., the process cannot be performed at −80.9° C. Accordingly, since the feed stream containing C1 and C2 hydrocarbon compounds to be fed to the gas-liquid separator FT after passing through the heat exchanger HE is not sufficiently condensed, the purification of the bottom discharge stream and the overhead discharge stream of the gas-liquid separator FT are also not performed at the above temperature and the pressure.

Therefore, in a case where the process flow diagram illustrated in FIG. 1 is applied in a real process rather than the simulation in which conditions that the process can be operated are set, there is problem in that the condensation in the heat exchanger HE is not sufficient, and the non-condensed fluid is discharged together with the overhead discharge stream of the gas-liquid separator FT and is introduced into the cold box CB. In addition, the cold box CB lacks energy for performing the cooling circulation due to the fluid introduced into the cold box CB. Thus, a serious loss in which ethylene which is a product is discharged through a tail gas occurs. In addition, the amount of fluid reintroduced into the second compressor P2 is increased by Joule-Thomson recycle in the cold box CB, therefore the amount of work is increased, resulting in the occurrence of the overload over the entire cold box CB.

The inventors of the present invention was found from the above results that in a case where ethylene is produced according to the present invention, it is possible to cope with a change in cracking yield depending on a change in feedstock, such that an additional gas furnace in which a gas phase feedstock is used may be freely installed, and may be individually operated even in a case where the liquid phase decomposition step in which naphtha is used is interrupted due to maintenance of process equipment. In addition, it was confirmed that since the amount of work increasing in proportion to a production amount was relatively reduced while increasing yield of ethylene by addition of a feedstock, it was possible to produce ethylene with less energy consumption even though a content of methane in the thermally compressed stream was increased.

The invention claimed is:

1. A method for preparing ethylene comprising:
   feeding a thermally cracked compressed stream to a first distillation apparatus;
   operating the first distillation apparatus as a first deethanizer when the thermally cracked compressed stream has a C1 hydrocarbon compound content of less than 20 mol%, feeding an overhead discharge stream of the first distillation apparatus to a second distillation apparatus, and feeding a bottom discharge stream of the second distillation apparatus to a C2 separator; and
   switching the operation of the first distillation apparatus to a first depropanizer when the thermally cracked compressed stream has a C1 hydrocarbon compound content of more than 20 mol%, feeding the overhead discharge stream of the first distillation apparatus to the second distillation apparatus, and feeding the bottom discharge stream of the second distillation apparatus through a third distillation apparatus to the C2 separator.

2. The method for preparing ethylene of claim 1, wherein the overhead discharge stream of the first deethanizer contains hydrogen and C1 and C2 hydrocarbon compounds when the first distillation apparatus is operated as the first deethanizer.

3. The method for preparing ethylene of claim 1, wherein the overhead discharge stream of the depropanizer contains hydrogen and C1, C2, and C3 hydrocarbon compounds when the first distillation apparatus is operated as the first depropanizer.

4. The method for preparing ethylene of claim 1, further comprising:
   feeding the overhead discharge stream of the first distillation apparatus to a second compressor;
   feeding a compressed discharge stream of the second compressor to an acetylene converter; and
   feeding a bottom discharge stream of the acetylene converter to the second distillation apparatus.

5. The method for preparing ethylene of claim 1, wherein the second distillation apparatus is a demethanizer, and the third distillation apparatus is a second deethanizer.

6. The method for preparing ethylene of claim 1, wherein an overhead discharge stream of the second distillation apparatus is circulated to a cold box.

7. The method for preparing ethylene of claim 1, wherein the bottom discharge stream of the second distillation apparatus is fed to the third distillation apparatus, and an overhead discharge stream of the third distillation apparatus is fed to the C2 separator when the first distillation apparatus is operated as the first depropanizer.

8. The method for preparing ethylene of claim 1, wherein an overhead discharge stream of the third distillation apparatus is a mixture of C2 hydrocarbon compounds.

9. The method for preparing ethylene of claim 1, wherein a bottom discharge stream of the third distillation apparatus is a mixture of C3 hydrocarbon compounds.

10. The method for preparing ethylene of claim 1, wherein an overhead discharge stream of the C2 separator is fed to a first compressor.

11. The method for preparing ethylene of claim 1, wherein a bottom discharge stream of the C2 separator is circulated as a feedstock.

* * * * *